United States Patent [19]

Smith et al.

[11] Patent Number: 4,687,774

[45] Date of Patent: Aug. 18, 1987

[54] METHOD FOR SUPPRESSING THE IMMUNE RESPONSE

[75] Inventors: Sidney R. Smith, Ridgewood; Marvin I. Siegel, Woodbridge, both of N.J.

[73] Assignee: Schering Corporation, Kenilworth, N.J.

[21] Appl. No.: 836,357

[22] Filed: Mar. 10, 1986

[51] Int. Cl.$^4$ ...................... A61K 31/44; A61K 31/50
[52] U.S. Cl. .................................. 514/293; 514/250; 514/885
[58] Field of Search ........................ 514/250, 293, 885

[56] References Cited

U.S. PATENT DOCUMENTS 4,596,809 6/1986 Sherlock .

*Primary Examiner*—Leonard Schenkman
*Attorney, Agent, or Firm*—Richard C. Billups; James R. Nelson; Stephen I. Miller

[57] ABSTRACT

A method and composition for suppressing the immune response are disclosed which employ an immunosuppressing effective amount of certain tricyclic naphthyridine or pyrido-pyrazine derivatives.

18 Claims, No Drawings

METHOD FOR SUPPRESSING THE IMMUNE RESPONSE

BACKGROUND OF THE INVENTION

The present invention relates to the use of certain tricyclic naphthyridine or pyrido-pyrazine derivatives in suppressing the immune response.

SUMMARY OF THE INVENTION

The present invention is drawn to a method for suppressing the immune response in a mammal which comprises administering to a mammal in need of such treatment an immunosuppressing effect amount of a compound having the structural formulae:

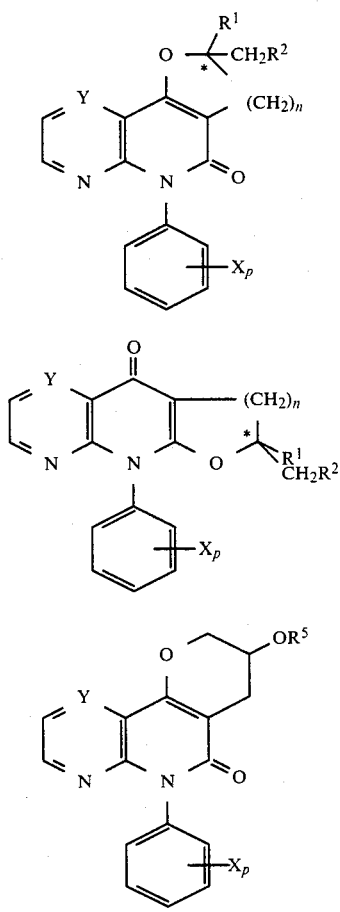

wherein
n is 1 or 2;
$R^1$ and $R^2$ may be combined to form a bond, or $R^1$ is hydrogen and $R^2$ is OR, halogen or $NR^3R^4$;
R is hydrogen, carboxylic acyl having from 2 to 10 carbon atoms, or carbamoyl;
$R^3$ and $R^4$ may be the same or different and each is independently hydrogen or alkyl having from 1 to 6 carbon atoms, or $R^3$ and $R^4$ may be combined with the nitrogen to which they are attached to form a pyrrolidino, piperidino, morpholino, or piperazino ring;
$R^5$ is hydrogen or carboxylic acyl having from 2 to 10 carbon atoms;
each X substituent is independently selected from hydroxy, alkyl having 1 to 6 carbon atoms, alkoxy having from 1 to 6 carbon atoms, nitro, halo, trifluoromethyl, alkyl—S(O)$_m$— having from 1 to 6 carbon atoms and wherein m is 0, 1 or 2;
p is 0, 1, 2 or 3; and
Y is CH or N;
and pharmaceutically acceptable salts thereof.

Preferred are compounds of formulae I or II, with compounds of formula I being more preferred.

Preferred compounds of formulae I and II are those wherein n is 1.

A third group of preferred compounds is that wherein Y is CH.

A fourth group of preferred compounds is that wherein $R^1$ is hydrogen and $R^2$ is OR wherein R is hydrogen or carboxylic acyl.

Still another group of preferred compounds is that wherein X is hydrogen or meta-halogeno. A preferred meta-halogeno group is meta-chloro.

DESCRIPTION OF THE INVENTION

As used herein, the term "carboxylic acyl" refers to the radical obtained by removing the hydroxyl group from the corresponding carboxylic acid, i.e. radicals of the formula

wherein $R^6$ is for example alkyl of 1 to 9 carbon atoms, phenyl, substituted phenyl wherein the substituents are as defined for X, benzyl, alkenyl of 2 to 7 carbon atoms or alkynyl of 2 to 7 carbon atoms. Similarly, "carbamoyl" refers to the radical obtained by removing the hydroxy group from the corresponding carbamic acid, i.e. radicals of the formula

wherein $R^7$ and $R^8$ are independently hydrogen, lower alkyl having from 1 to 6 carbon atoms, and hydroxyalkyl having from 1 to 6 carbon atoms.

It is contemplated that there may be 1 to 3 "X" substituents on the phenyl ring. As used herein, the term "alkyl" (including the "alk" portion of alkoxy) refers to straight or branched chain groups, e.g. methyl, ethyl, propyl, isopropyl, butyl, isobutyl and hexyl. Examples of "alkoxy" groups are methoxy, ethoxy, isopropoxy, butoxy and hexoxy. "Halo" refers to fluoro, chloro, bromo and iodo.

The term "pharmaceutically acceptable salts" as used herein refers to salts formed with acids such as hydrochloric, hydrobromic, methanesulfonic and sulfuric acids.

The compounds of formulae I and II wherein $R^1$ is hydrogen have at least one asymmetric carbon atom, i.e., the carbon indicated with an asterisk(*) in formulae I and II. The compounds accordingly exist in enantiomeric forms or in racemic mixtures thereof, and all such isomers and racemic mixtures are within the scope of this invention. Separation of the isomers may be accomplished by methods well known to those skilled in the art.

The compounds of formulae I, II and III can exist in unsolvated as well as solvated forms, including hydrated forms. In general, the solvated forms, with pharmaceutically acceptable solvents such as water, ethanol and the like are equivalent to the unsolvated forms for purposes of the invention.

Representative compounds of formulae I, II and III are exemplified below in Table I:

TABLE I

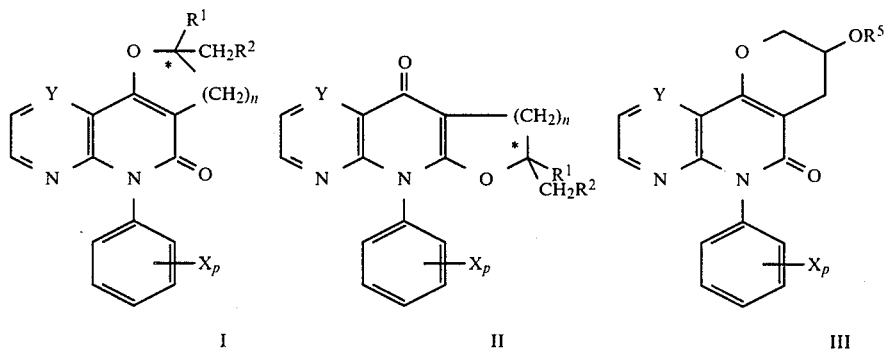

| Compound No. | Formula No. | Y | (Xp)=[1] | n | $R^1$ | $R^2$ | $R^5$ | m.p. (°C.) |
|---|---|---|---|---|---|---|---|---|
| 1 | I | CH | — | 1 | H | —OH | — | 267–268 |
| 2 | I | CH | 3-Cl | 1 | H | —OH | — | |
| 3 | I | CH | — | 1 | H | —OOCCH$_3$ | — | 204–206 |
| 4 | I | CH | 3-CH$_3$O— | 1 | H | —OOCCH$_3$ | — | 183–184 |
| 5 | I | CH | — | 1 | H | —I | — | 238–240 |
| 6 | I | CH | 3-CH$_3$O— | 1 | H | —I | — | 238–240 |
| 7 | I (hemihydrate) | CH | — | 1 | H | —N⟨pyrrolidine⟩ | — | 178–179 |
| 8 | I (hydrochloride) | CH | — | 1 | H | —N⟨piperidine⟩ | — | 278–279 |
| 9 | II | CH | — | 1 | H | —Br | — | 187–188 |
| 10 | II (hydrochloride, ¾ hydrate) | CH | — | 1 | H | —N⟨pyrrolidine⟩ | — | 187–190 |
| 11 | II | CH | 3-CH$_3$O— | 1 | H | —Br | — | |
| 12 | II | CH | — | 1 | H | —I | — | |
| 13 | II | CH | — | 1 | bond[2] | bond[2] | — | 259–261 |
| 14 | III | CH | — | — | — | — | —H | 296–298 |
| 15 | III | CH | — | — | — | — | —OCCH$_3$ | 224–226 |

[1] The "—" in this column indicates no substitution on the phenyl ring.
[2] ($R^1$)CH$_2$R$^2$ equals =CH$_2$.

The compounds employed this invention may be prepared by methods known to those skilled in the art. See U.S. application Ser. No. 716,003 filed Mar. 25, 1985 (now U.S. Pat. No. 4,596,809), the disclosure of which is incorporated herein by reference. An example of such a method for preparing compounds of formulae I and III wherein Y is CH is shown in the following reaction scheme:

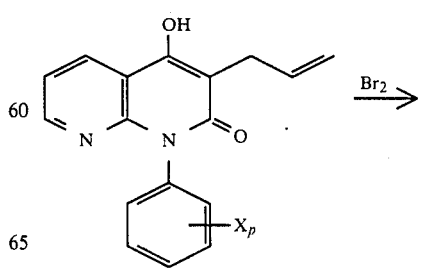

IV

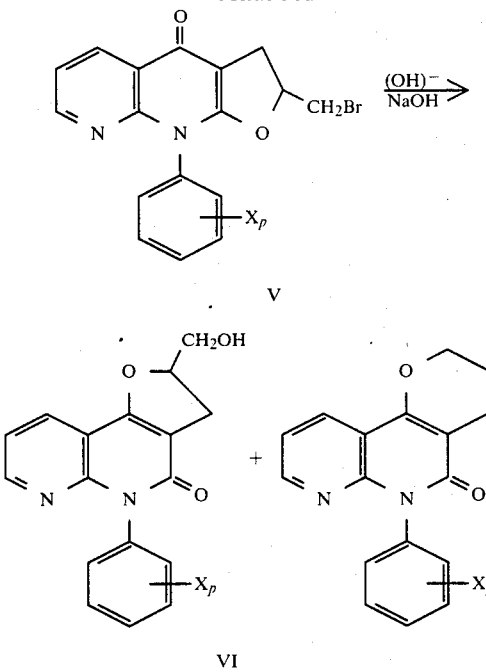

-continued

V

VI    VII wherein X is as defined above. In the above scheme, bromination of the starting material of formula IV results in the spontaneous cyclization of the intermediate dibromo compound to the compound of formula V. In the presence of aqueous sodium hydroxide, the compound of formula V undergoes hydrolysis to yield compounds of formulae VI and VII.

An example of a method of preparing compounds of formula II wherein Y is CH and $R^2$ is $NR^3R^4$ is described in the following reaction scheme:

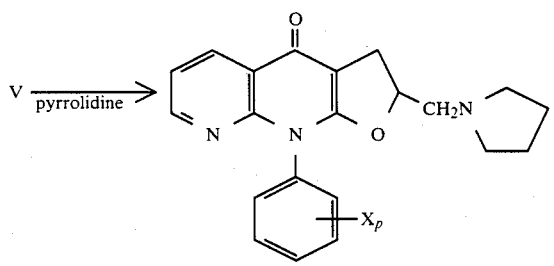

Compounds of formula IV may be prepared by methods known in the art. See, for example, U.S. Pat. No. 4,492,702.

Compounds of this invention wherein Y is N may be similarly prepared using starting materials analogous to the compounds of formula IV. That is, 2-phenylamino-3-pyrazine carboxylates may be used in place of 2-phenylamino-3-pyridine carboxylates to prepare pyrazino-pyridine compounds in place of naphthyridinones.

For the preparation of compounds of formulae I or II wherein $R^1$ is hydrogen and $R^2$ is OR wherein R is acyl and compounds of formula III wherein $R^5$ is acyl, standard acylation techniques may be used, e.g. refluxing the corresponding alcohol with an acid anhydride in an inert solvent such as benzene.

Compounds of formulae I or II wherein $R^2$ is $NR^3R^4$ may be prepared for example, through the reaction of the corresponding 2-halomethyl compound and the appropriate amine.

Compounds wherein $R^1$ and $R^2$ form a bond may also be prepared by standard techniques, e.g. by dehydrohalogenation of the halomethyl side chain in the presence of a base.

The compounds are useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(B6AF1) male mice were injected intravenously with parental (C57B1/6J) spleen and lymph node cells. The compound 3,5-dihydro-2-hydroxymethyl-5-phenyl-furo(3,2-c)-1,8-naphthyridin-4-(2H)-one (Compound A) was then administered orally for 10 days beginning on the day prior to the cell transfer. On the day following the last treatment, the animals were sacrificed, and their spleens were excised and weighed. The enlargement of the spleen of the host is a result of a GVHR. To some extent it is the host's own cells which infiltrate and enlarge the spleen although they do this because of the present of graft cells reacting against the host. The amount of spleen enlargement, splenomegaly, is taken as a measure of the severity of the GVHR.

In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of Compound A administered to the mice in the experimental group is measured by comparing the spleen weight of the untreated and treated GVH animal with that of the syngeneic control. In this test Compound A reduced spleen weight by 138% as compared to the untreated animals at a dose of 100 mg/kg.

SPLENIC ATROPHY

The immunosuppressive activity of the compounds may also be shown by a decrease in spleen weight after dosing $BDF_1$ mice orally with the drug for seven (7) consecutive days. The mice are sacrificed on the eighth day. The percent decrease in spleen weight is measured for each dosage level. In this procedure Compound A provided a 25% and 48% spleen weight decrease at a dosages level of 25 mg/kg and 50 mg/kg, respectively, indicating an $ED_{30}$ of between 25 mg/kg and 50 mg/kg.

The subject compounds also possess anti-allergy and anti-inflammatory activities. For example, Compound A has an $ED_{50}$ value of below about 2 mg/kg p.o. in tests measuring the inhibition of anaphylactic bronchospasm in sensitized guinea pigs having antigen-induced bronchoconstriction and an $ED_{50}$ value of below about 25 mg/kg p.o. in tests measuring the reverse passive Arthus reaction in the paw of rats (as described by in copending U.S. application Ser. No. 716,003 filed Mar. 25, 1985). These results for Compound A indicate that an immunosuppressive effective dose for the copounds of formulae I, II and III is about 5 times or more their anti-allergy effective doses ($ED_{50s}$).

The usual dosage range for the compounds of formulae I, II and III in a 70 kg mammal is an oral dose of about 0.1 to 250 mg/kg, preferably 0.1 to 150 mg/kg, in 3 or 4 divided doses per day. Of course, the dose will be regulated according to the potency of compound employed, the immunological disease being treated, and the judgment of the attending clinician depending on factors such as the degree and the severity of the disease state and age and general condition of the patient being treated.

To treat immunological diseases, the active compounds of formulae I, II and III can be administered in unit dosage forms such as tablets, capsules, pills, powders, granules, sterile parenteral solutions or suspensions, suppositories, transdermal compositions and the like. Such dosage forms are prepared according to standard techniques well known in the art.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium strearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution or suspension in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in additions to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well the mixtures thereof. Naturally, the solvent utilized will be chosen with regard to the route of administration, for example, liquid preparations containing large amounts of ethanol are not suitable for parenteral use.

The composition of the invention may also be deliverable transdermally. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be appropriate number of any of these in packaged form. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following Examples are intended to illustrate, but not to limit, the present invention. In the Examples the term "Compound A" refers to 3,5-dihydro-2-hydroxymethyl-5-phenyl-furo(3,2-c)-1,8-naphthyridin-4(2H)-one. It is contemplated, however, that this compound may be replaced by equally effective quantities of other compounds of formulae I, II or III as defined above.

EXAMPLE 1

| No. | Ingredient | Tablets mg/tablet | mg/tablet |
|---|---|---|---|
| 1 | Compound A | 100 | 500 |
| 2 | Lactose USP | 122 | 113 |
| 3 | Corn Starch, Food Grade, as a 10% paste in | 30 | 40 |

| | Tablets | | |
|---|---|---|---|
| No. | Ingredient | mg/tablet | mg/tablet |
| | Purified Water | | |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., $\frac{1}{4}''$) if needed. Dry the damp granules. Screen the dried granules if needed and mix with the Items No. 4 and mix for 10–15 minutes. Add Item No. 5 and mix for 1–3 minutes. Compress the mixture to appropriate the size and weight on a suitable tablet machine.

EXAMPLE 2

| | Capsules | | |
|---|---|---|---|
| No. | Ingredient | mg/capsule | mg/capsule |
| 1. | Compound A | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE 3

| | Parenteral | |
|---|---|---|
| Ingredient | mg/vial | mg/vial |
| Compound A Sterile Powder | 100 | 500 |

Add sterile water for injection or bacteriostatic water for injection, for reconstitution.

EXAMPLE 4

| | Injectable | | |
|---|---|---|---|
| No. | Ingredient | mg/vial | mg/vial |
| 1. | Compound A | 100 | 500 |
| 2. | Methyl para-hydroxybenzoate | 1.8 | 1.8 |
| 3. | Propyl para-hydroxybenzoate | 0.2 | 0.2 |
| 4. | Sodium Bisulfite | 3.2 | 3.2 |
| 5. | Disodium Edetate | 0.1 | 0.1 |
| 6. | Sodium Sulfate | 2.6 | 2.6 |
| 7. | Water for Injection q.s. ad | 1.0 ml | 1.0 ml |

Method for Manufacture

1. Dissolve the hydroxybenzoate compounds in a portion (85% of the final volume) of the water for injection at 65°–70° C.
2. Cool to 25°–35° C. Charge and dissolve the sodium bisulfite, disodium edetate and sodium sulfate.
3. Charge and dissolve drug.
4. Bring the solution to final volume by added water for injection.
5. Filter the solution through 0.22 membrane and fill into appropriate containers.
6. Finally sterilize the units by autoclaving.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method of suppressing the immune response in a mammal which comprises administering to a mammal in need of such treatment an immunosuppressing effective amount of a compound having the structural formulae I, II or III:

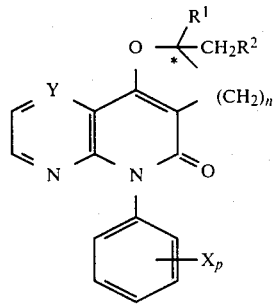

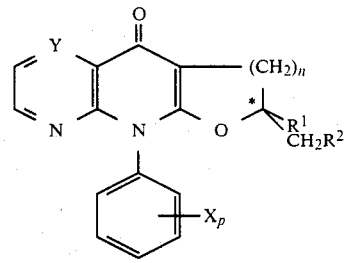

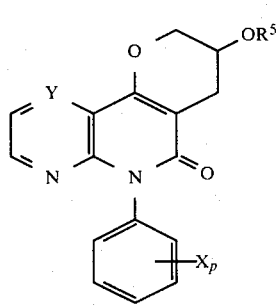

or pharmaceutical acceptable salt thereof, wherein n is 1 or 2;

$R^1$ and $R^2$ may be combined to form a bond, or $R^1$ is hydrogen and $R^2$ is OR, halogen or $NR^3R^4$;

R is hydrogen, carboxylic acyl having from 2 to 10 carbon atoms, or carbamyl;

$R^3$ and $R^4$ may be the same or different and each is independently hydrogen or alkyl having from 1 to 6 carbon atoms, or $R^3$ and $R^4$ may be combined with the nitrogen to which they are attached to form a pyrrolidino, piperidino, morpholino, or piperazino ring;

$R^5$ is hydrogen or carboxylic acyl having from 2 to 10 carbon atoms;

each X substituent is independently selected from hydroxy, alkyl having 1 to 6 carbon atoms, alkoxy having from 1 to 6 carbon atoms, nitro, halogen, trifluoromethyl, or alkyl—S(O)$_m$ having from 1 to 6 carbon atoms and wherein m is 0, 1 or 2;

p is 0, 1, 2 or 3; and

Y is CH or N.

2. A method according to claim 1 wherein said compound is represented by formula I.

3. A method according to claim 1 wherein Y in formulae I, II and III is CH.

4. A method according to claim 1 wherein said compound is represented by formula I and Y is CH.

5. A method according to claim 4 wherein n in formula I is 1.

6. A method according to claim 4 wherein $R^1$ and $R^2$ in formula I are combined to form a bond.

7. A method according to claim 4 wherein $R^1$ in formula I is hydrogen.

8. A method according to claim 7 wherein $R^2$ in formula I is OR.

9. A method according to claim 8 wherein R in formula I is hydrogen.

10. A method according to claim 8 wherein R in formula I is carboxylic acyl.

11. A method according to claim 8 wherein R in formula I is carbamyl.

12. A method according to claim 7 wherein $R^2$ in formula I is halogen.

13. A method according to claim 7 wherein $R^2$ in formula I is $NR^3R^4$.

14. A method according to claim 1 wherein said compound is selected from 3,5-dihydro-2-(hydroxymethyl)-5-phenyl-furo(3,2-c)-1,8-naphthyridin-4(2H)-one, 5-(3-chlorophenyl)-3,5-dihydro-2-(hydroxymethyl)-furo(3,2-c)-1,8-naphthyridin-4(2H)-one, 2-(acetyloxymethyl)-3,5-dihydro-5-phenylfuro(3,2-c)-1,8-naphthyridin-4(2H)-one, 2-(acetyloxymethyl)-3,5-dihydro-5-(3-methoxyphenyl)-furo(3,2-c)-1,8-naphthyridin-4(2H)-one, 3,5-dihydro-2-(iodomethyl)-5-phenyl-furo(3,2-c)-1,8-naphthyridin-4(2H)-one, 3,5-dihydro-2-(iodomethyl)-5-(3-methoxyphenyl)-furo(3,2-c)-1,8-naphthyridin-4(2H)-one, 3,5-dihydro-5-phenyl-2-(1-pyrrolidinylmethyl)furo(3,2-c)-1,8-naphthyridin-4-(2H)-one, 3,5-dihydro-5-phenyl-2-(1-piperidinylmethyl)furo(3,2-c)-1,8-naphthyridin-4-(2H)-one, 2-(bromomethyl)-3,9-dihydro-9-phenyl-furo(2,3-b)-1,8-naphthyridin-4(2H)-one, 3,9-dihydro-9-phenyl-2-(1-pyrrolidinylmethyl)furo(2,3-b)-1,8-naphthyridin-4(2H)-one, 2-(bromomethyl)-3,9-dihydro-9-(3-methoxyphenyl)-furo(2,3-b)-1,8-naphthyridin-4(2H)-one, 3,9-dihydro-2-(iodomethyl)-9-phenyl-furo(2,3-b)-1,8-naphthyridin-4(2H)-one, 3,9-dihydro-2-methylene-9-phenylene-furo(2,3-b)-1,8-naphthyridin-4(2H)-one, 3-hydroxy-6-phenyl-2,3,4,6-tetrahydro-5H-pyrano(3,2-c)-1,8-naphthyridin-5-one, or 3-acetyloxy-6-phenyl-2,3,4,6-tetrahydro-5H-pyrano(3,2-c)-1,8-naphthyridin-5-one, or a pharmaceutically acceptable salt thereof.

15. A method according to claim 4 wherein said compound is 3,5-dihydro-2-(hydroxymethyl)-5-phenyl-furo[3,2-c]-1,8-naphthyridin-4(2H)-one.

16. A method according to claim 4 wherein said compound is 2-(acetyloxymethyl)-3,5-dihydro-5-phenyl-furo[3,2-c]-1,8-naphthyridin-4(2H)-one.

17. A method according to claim 1 wherein the compound is administered orally.

18. A method according to claim 15 wherein the compound is administered orally.

* * * * *